(12) United States Patent
Weitzner et al.

(10) Patent No.: US 11,439,417 B2
(45) Date of Patent: Sep. 13, 2022

(54) NECROSECTOMY DEVICES AND PROCEDURES

(71) Applicant: Boston Scientific Scimed, Inc., Maple Grove, MN (US)

(72) Inventors: Barry Weitzner, Acton, MA (US); Ryan Hartman, Kingston, MA (US); Peter L. Dayton, Brookline, MA (US); John B. Golden, Norton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 239 days.

(21) Appl. No.: 15/876,676

(22) Filed: Jan. 22, 2018

(65) Prior Publication Data

US 2018/0206864 A1 Jul. 26, 2018

Related U.S. Application Data

(60) Provisional application No. 62/449,526, filed on Jan. 23, 2017.

(51) Int. Cl.
*A61B 17/221* (2006.01)
*A61B 17/32* (2006.01)
(Continued)

(52) U.S. Cl.
CPC ...... *A61B 17/221* (2013.01); *A61B 17/00234* (2013.01); *A61B 17/3203* (2013.01); *A61B 17/320016* (2013.01); *A61B 17/320725* (2013.01); *A61B 17/320758* (2013.01); *A61M 1/84* (2021.05); *A61M 25/09* (2013.01); *A61B 2017/00358* (2013.01); *A61B 2017/00557* (2013.01); *A61B 2017/00818* (2013.01); *A61B 2017/22061* (2013.01);
(Continued)

(58) Field of Classification Search
CPC .............. A61B 17/221; A61B 17/3203; A61B 17/320725; A61B 17/320758; A61B 17/00234; A61B 17/320016; A61B 2017/22061; A61B 2017/320004; A61B 2017/320733; A61B 2017/320008; A61B 2017/00358
See application file for complete search history.

(56) References Cited

U.S. PATENT DOCUMENTS 4,445,509 A 5/1984 Auth
4,750,902 A 6/1988 Wuchinich et al.
(Continued)

FOREIGN PATENT DOCUMENTS

DE 3421390 12/1985
WO 9601079 1/1996
WO 200141656 6/2001

OTHER PUBLICATIONS

International Search Report and Written Opinion dated May 8, 2018, for PCT/US18/14659 (19 pages).

*Primary Examiner* — Bradley J Osinski
(74) *Attorney, Agent, or Firm* — Seager, Tufte & Wickhem LLP

(57) ABSTRACT

The present disclosure relates generally to the field of minimally invasive catheter-based devices and procedures for the removal of necrotic debris. In particular, the present disclosure relates to systems and methods for the removal of necrotic debris from within a walled off necrosis without disrupting or damaging the tissue wall of the necrotic pocket.

17 Claims, 8 Drawing Sheets

(51) Int. Cl.
  *A61M 25/09* (2006.01)
  *A61B 17/00* (2006.01)
  *A61B 17/3207* (2006.01)
  *A61B 17/3203* (2006.01)
  *A61M 1/00* (2006.01)
  A61B 17/22 (2006.01)
  A61B 90/00 (2016.01)

(52) U.S. Cl.
  CPC ............... *A61B 2017/22079* (2013.01); *A61B 2017/320004* (2013.01); *A61B 2017/320008* (2013.01); *A61B 2017/320733* (2013.01); *A61B 2090/08021* (2016.02)

(56) References Cited

U.S. PATENT DOCUMENTS

| | | | |
|---|---|---|---|
| 5,071,424 A * | 12/1991 | Reger | A61B 17/32075 606/159 |
| 5,665,098 A * | 9/1997 | Kelly | A61B 17/32075 604/22 |
| 5,766,194 A | 6/1998 | Smith | |
| 5,785,848 A | 7/1998 | Strand | |
| 6,319,242 B1 * | 11/2001 | Patterson | A61B 17/3207 604/508 |
| 7,291,146 B2 * | 11/2007 | Steinke | A61B 18/1492 606/41 |
| 7,655,016 B2 * | 2/2010 | Demarais | A61B 17/320725 606/159 |
| 8,632,557 B2 * | 1/2014 | Thatcher | A61B 17/320758 606/159 |
| 2004/0193046 A1 | 9/2004 | Nash et al. | |
| 2007/0208370 A1 * | 9/2007 | Hauser | A61F 2/01 606/200 |
| 2009/0076409 A1 * | 3/2009 | Wu | A61N 1/36017 600/547 |
| 2011/0112434 A1 * | 5/2011 | Ghabrial | A61B 1/00135 600/564 |
| 2013/0103063 A1 * | 4/2013 | Escudero | A61B 17/320758 606/159 |
| 2015/0257825 A1 * | 9/2015 | Kelly | A61B 18/1492 606/41 |

* cited by examiner

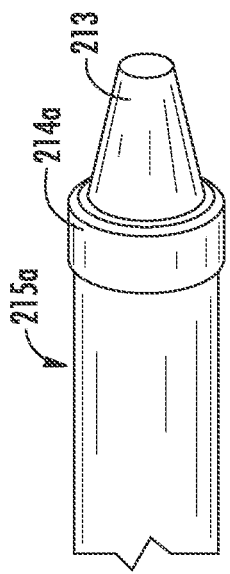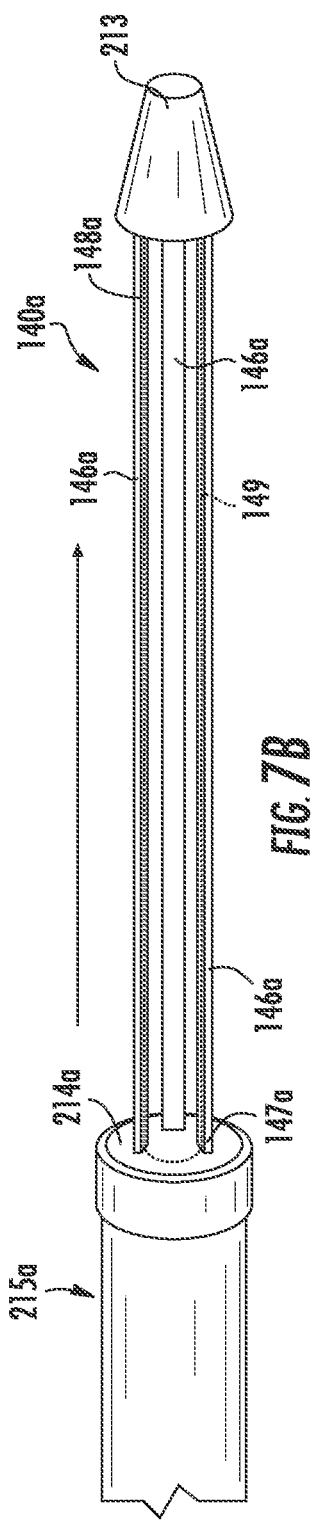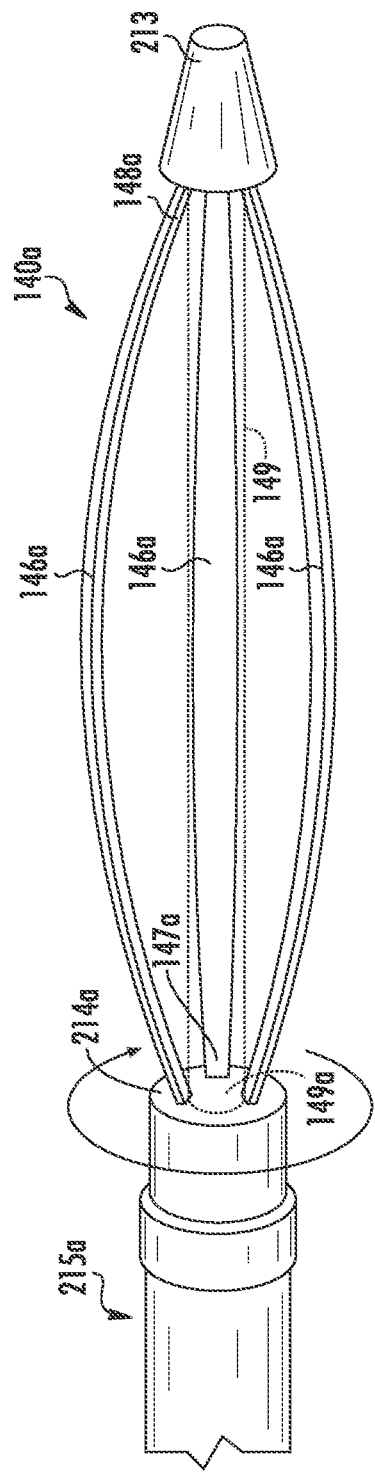

NECROSECTOMY DEVICES AND PROCEDURES

CROSS REFERENCE TO RELATED APPLICATIONS

The present application claims the benefit of priority under 35 U.S.C § 119 to U.S. Provisional Patent Application Ser. No. 62/449,526, filed on Jan. 23, 2017, which is incorporated by reference in its entirety for all purposes.

FIELD

The present disclosure relates generally to the field of minimally invasive catheter-based devices and procedures for the removal of necrotic debris. In particular, the present disclosure relates to systems and methods for the removal of necrotic debris from within a walled-off necrosis without disrupting or damaging the tissue wall of the necrotic pocket.

BACKGROUND

A walled-off pancreatic fluid collection, also referred to as walled-off pancreatic necrosis (WOPN), typically occurs as a complication following acute pancreatitis, chronic pancreatitis or pancreatic trauma, which leads to necrosis and subsequent liquefaction of pancreatic and/or peripancreatic tissues. A WOPN may become infected and/or cause mass effect (e.g., press against the biliary system and cause upstream swelling). Management protocols are typically dictated by the location of the WOPN and the patient's symptoms. Approximately 40% of WOPN's are asymptomatic and resolve spontaneously without medical intervention. However, symptomatic patients typically require surgical intervention to drain the necrotic debris from the WOPN. The consistency of the necrotic debris within the WOPN tends to vary dramatically between individuals, with thicker and more viscous necrotic debris requiring a more aggressive interventional procedure using, e.g., a wide-bore drainage catheter. An important factor that must be considered when removing this necrotic debris is the presence of shallow blood vessels, which tend to line the tissue wall of the WOPN. Rupture of these vessels and/or the tissue wall itself may cause a dangerous and potentially fatal bleeding event.

A variety of advantageous medical outcomes may be realized by the systems and/or methods of the present disclosure, which allows efficient removal of necrotic debris, e.g., of varying consistency from a WOPN without disrupting or damaging the tissue wall and/or blood vessels therein.

SUMMARY

The present disclosure, in its various aspects, provides advantages in the field of minimally invasive catheter-based devices and procedures for the removal of necrotic debris including body lumen drainage with an integrated medical device for the removal of necrotic debris from within a walled-off necrosis without disrupting or damaging the tissue wall of the necrotic pocket.

In one aspect, the present disclosure relates to a system comprising an elongate member which includes a distal end, a proximal end, and at least one fluid delivery lumen extending therebetween. At least one fluid delivery aperture is disposed on a distal portion of the elongate member, wherein the at least one fluid delivery aperture is in fluid communication with the fluid delivery lumen. The at least one fluid delivery aperture may include at least one fluid delivery aperture disposed on the distal end of the elongate member. In addition, or alternatively, the at least one fluid delivery aperture may include a plurality of side-facing fluid delivery apertures radially disposed about a circumference of the distal portion of the elongate member. In addition, or alternatively, the at least one fluid delivery aperture may include a plurality of rear-facing fluid delivery apertures radially disposed about a circumference of the distal portion of the elongate member. In addition, or alternatively, the distal portion of the elongate member may include a recessed portion, wherein the at least one fluid delivery aperture includes a plurality of inward-facing fluid delivery apertures. The system may further include an arm extending distally beyond the distal end of the elongate member, wherein the arm includes a planar surface facing the at least one distal end fluid delivery aperture. The planar surface may be positioned such that a fluid flowing through the at least one distal end fluid delivery aperture impacts the planar surface. The elongate member may include a circumferential recessed portion proximal to the rear-facing fluid delivery apertures, the circumferential recessed portion may define a planar surface facing the rear-facing fluid delivery apertures. The planar surface may be positioned such that a fluid flowing through the rear-facing fluid delivery apertures impacts the planar surface. The fluid delivery lumen and fluid delivery aperture may be configured to deliver fluid therethrough as a high-pressure jet. A diameter of the fluid delivery lumen, or a portion thereof, may be varied to adjust the velocity of the high-pressure jet. A diameter of an opening of at least one fluid delivery aperture may be varied to adjust the velocity of the high-pressure jet. The elongate member may further include a removal lumen extending between the proximal and distal ends thereof. The elongate member may be configured to be delivered through the working channel of an endoscope. The elongate member may further include a camera disposed on the distal portion thereof.

In another aspect, the present disclosure relates to a system comprising an elongate member which includes a distal end, a proximal end and a tissue disrupting element on the distal end. The tissue disrupting element may include a cage and a cutting element rotationally disposed within the cage. The tissue disrupting element includes a plurality of cutting members disposed around a support shaft, and wherein each of the plurality of cutting members includes a proximal end attached to a proximal end of the support shaft, and a distal end attached to a distal end of the support shaft. The tissue disrupting element may include a plurality of cutting members, wherein a proximal end of each cutting member is attached to the distal end of the elongate member and a distal end of each cutting element is unattached and extends distally beyond the distal end of the elongate member. In addition, or alternatively, the tissue disrupting element may include at least one grasping element, wherein each grasping element includes two or more arms moveable between an open configuration and a closed configuration. In addition, or alternatively, the tissue disrupting element may include an expandable member having a course outer surface.

In yet another aspect, the present disclosure relates to a drainage catheter comprising a first tubular portion, a second tubular portion, and a third tubular portion. The first and second tubular portions may define a fluid delivery lumen, and the second and third tubular portions may define a bifurcated fluid removal lumen. A diameter of the fluid delivery lumen may be less than a diameter of the fluid removal lumen.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 7A-7C provide perspective views of a necrosectomy tool comprising a plurality of cutting elements configured to move between a delivery configuration (FIG. 7B) and deployed configuration (FIG. 7C), according to one embodiment of the present disclosure.

DETAILED DESCRIPTION

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to the removal of necrotic debris from within a walled-off pancreatic necrosis, the systems described herein may be used to flush, clean or debride a variety of body lumens, vessels, organs and/or structures, including, but not limited to cysts, pseudocysts and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Flow Disruptors

In one embodiment, the present disclosure relates to a necrosectomy tool which utilizes a flow of liquid (e.g., pulsed water-jet flow, etc.) to facilitate disruption and removal of necrotic debris and fluid without disrupting or damaging the tissue wall of the necrotic pocket. The flow of liquid may be non-pulsed or pulsed. These flow disruptors may find beneficial use for removal of necrotic debris of various consistencies, including, but not limited to, low or medium viscosity necrotic debris (e.g., "flowable" necrotic debris) that does not necessarily require physical disruption to facilitate efficient clearance from the necrotic pocket.

Figure 1:
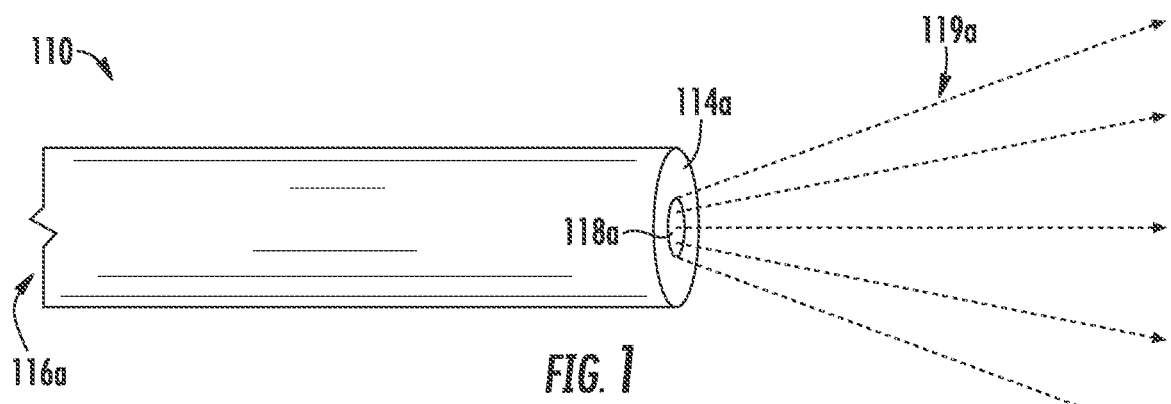
FIG. 1 provides a perspective view of a necrosectomy tool comprising a front-facing fluid delivery aperture, according to one embodiment of the present disclosure.

Referring to FIG. 1, a necrosectomy tool of the present disclosure may include an elongate member 110 comprising a proximal end (not shown), a distal end 114a and a fluid delivery lumen 116a extending therebetween. The distal end 114a may include a front-facing aperture 118a (e.g., port, opening, etc.) in fluid communication with the fluid delivery lumen 116a. The proximal end of the elongate member 110 may be fluidly connected to an external fluid source (not shown) configured to deliver pressurized fluid through the lumen 116a, e.g., such that fluid exits the front-facing aperture 118a as a high-pressure jet or spray 119a, to disrupt (e.g., facilitate movement, flow, circulation, etc.) and/or agitate the necrotic debris. Although the necrosectomy tool of FIG. 1 includes a single front-facing aperture 118a, in various embodiments the necrosectomy tool may include any number of front-facing apertures arranged in a variety of patterns about the distal end 114a.

Figure 2A:
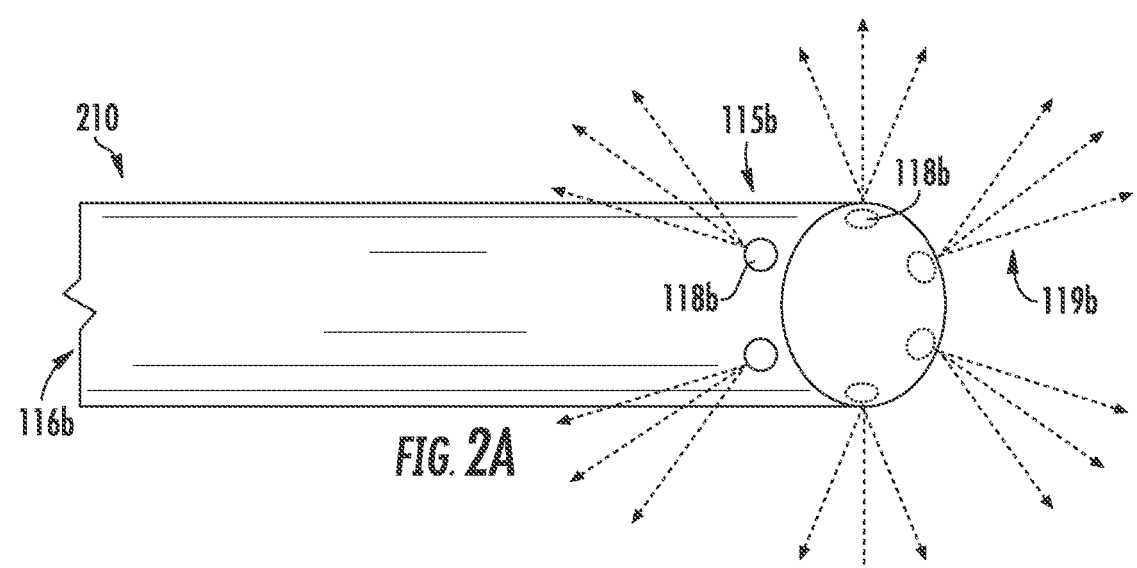
FIGS. 2A-2E provide a perspective view of a necrosectomy tool comprising one or more side-facing fluid delivery apertures, according to one embodiment of the present disclosure.
Figure 2B:
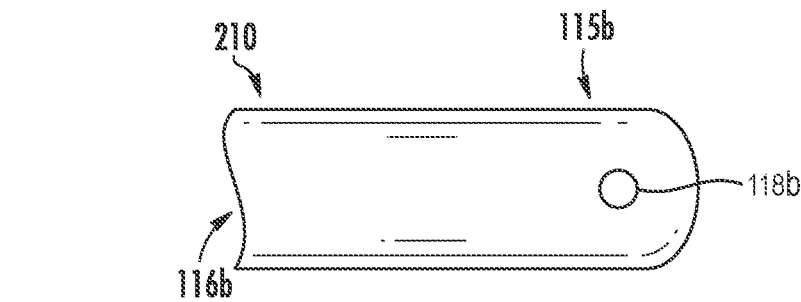
Figure 2C:
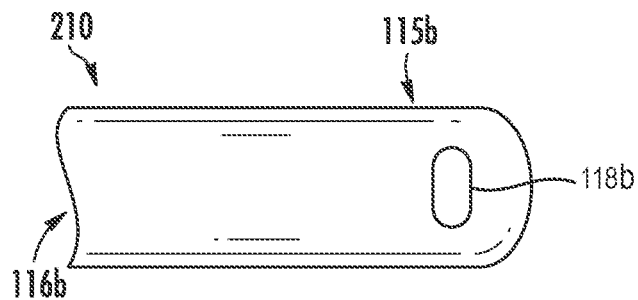
Figure 2D:
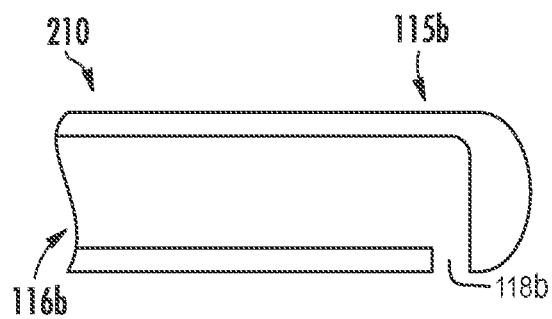
Figure 2E:
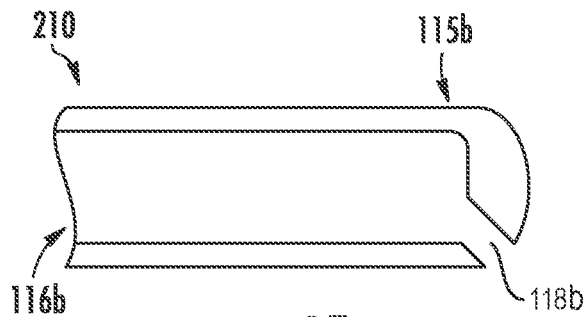

Referring to FIGS. 2A-2E, a necrosectomy tool of the present disclosure may, additionally or alternatively, include an elongate member 210 comprising one or more side-facing apertures 118b radially disposed about a distal portion 115b of the elongate member 210 and in fluid communication with the fluid delivery lumen 116b. The proximal end (not shown) of the elongate member may be fluidly connected to an external fluid (not shown) source configured to deliver pressurized fluid through the lumen 116b such that fluid exits the side-facing apertures(s) 118b substantially perpendicular to the longitudinal axis of the elongate member, e.g., as a high-pressure jet or spray 119b. Although the necrosectomy tool of FIG. 2A includes six side-facing apertures 118b in one plane evenly spaced about a circumference of the distal portion 115b, in various embodiments the elongate member 210 may include any number, arrangement, pattern and/or spacing of the side-facing apertures 118b about and along the distal portion 115b. For example, in various embodiments, the side-facing aperture 118b may include a single substantially circular (e.g., cylindrical, round, etc.) opening (FIG. 2B) or a single substantially horizontal (e.g., oblong) opening or slit (FIG. 2C). Referring to FIG. 2D, in one embodiment, the side-facing aperture(s) 118b of FIGS. 2A-2C may extend through the distal portion 115b of the elongate member 210 at an angle of approximately 90 degrees relative to the longitudinal axis of the elongate member. Referring to FIG. 2E, in another embodiment, the side-facing aperture(s) 118b of FIGS. 2A-2C may extend through the distal portion 115b of the elongate member 210 at an angle of approximately 45 degrees relative to the longitudinal axis of the elongate member. In various embodiments, the side-facing aperture(s) 118b may be positioned at a variety of additional angles (e.g., approximately 20 degrees, approximately 30 degrees, approximately 45 degrees, 55 degrees, 65 degrees, 75 degrees, etc.) along either side of the longitudinal axis of the elongate member to provide a broader or narrower stream of high-pressure fluid.

In use and by way of example, a necrosectomy tool of the present disclosure comprising a single side-facing aperture 118b may provide the medical professional with improved visibility of the distal portion 115b of the elongate member 210, e.g., as a pulsatile flow of the high-pressure jet or spray is delivered within the necrotic pocket, thereby facilitating efficient removal of debris and minimizing the likelihood of rupturing vessels on or within the tissue wall of the necrotic pocket.

Figure 3:
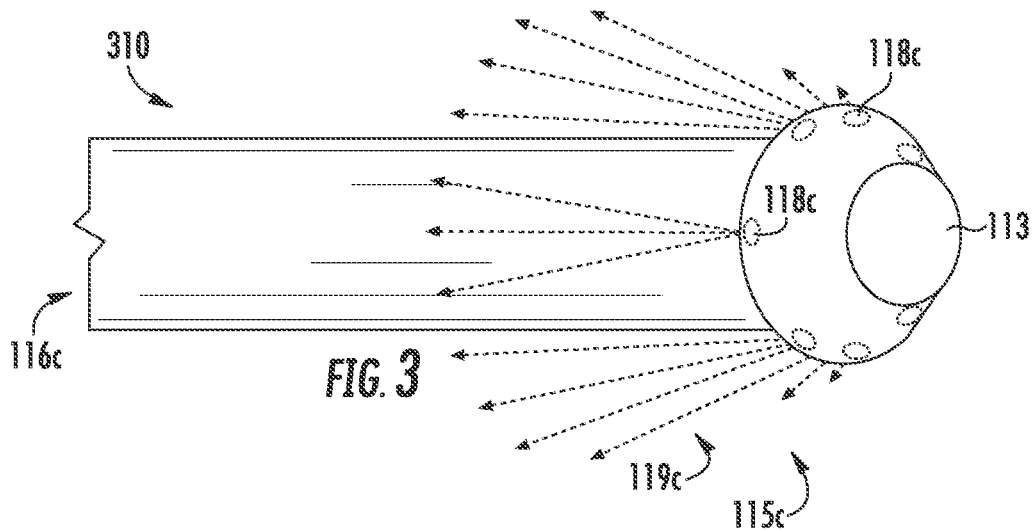
FIG. 3 provides a perspective view of a necrosectomy tool comprising rear-facing fluid delivery apertures, according to one embodiment of the present disclosure.

Referring to FIG. 3, a necrosectomy tool of the present disclosure may, additionally or alternatively, include an elongate member 310 comprising one or more rear-facing apertures 118c radially disposed about a distal portion 115c of the elongate member and in fluid communication with the fluid delivery lumen 116c. The proximal end (not shown) of the elongate member may be fluidly connected to an external fluid source (not shown) configured to deliver pressurized fluid through the lumen 116c such that fluid exits rear-facing apertures(s) 118c, e.g., as a high-pressure jet or spray 119c. In this and other embodiments, the distal end 114a of the elongate member may include an atraumatic tip 113 (e.g., rounded end) to further minimize or prevent trauma to the tissue wall of the necrotic pocket. The atraumatic tip 113, and the elongate member, may be formed from a variety of soft or compliant materials as are known in the art (e.g., soft plastics, soft rubber, neoprene, and the like). The rear-facing apertures and/or atraumatic tip may allow the necrosectomy tool to be placed in direct contact with the tissue wall of the necrotic pocket while protecting the underlying tissue from damage and/or encouraging the outward flow of necrotic debris (e.g., into the duodenum). Although the necrosectomy tool of FIG. 3 includes six rear-facing apertures 118c evenly spaced about a circumference of the distal portion 115c, in various embodiments the elongate member 310 may include any number, arrangement, pattern and/or spacing of rear-facing apertures 118c about the distal portion 115c. For example, the rear-facing aperture(s) may be positioned substantially parallel (e.g., approximately 90 degrees) relative to the longitudinal axis of the elongate member. The angle of the rear-facing aperture(s) may vary as necessary (e.g., approximately 70 degrees, approximately 80 degrees, approximately 100 degrees, approximately 110 degrees) to provide a broader or narrower stream of high-pressure fluid.

Figure 4:
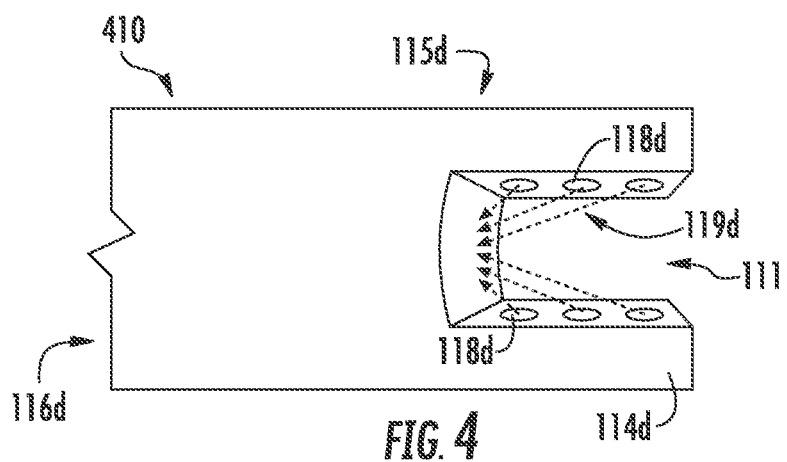
FIG. 4 provides a perspective view of a necrosectomy tool comprising inward-facing fluid delivery apertures, according to one embodiment of the present disclosure.

Referring to FIG. 4, a necrosectomy tool of the present disclosure may, additionally or alternatively, include an elongate member 410 comprising one or more inward-facing apertures 118d disposed within a recess or pocket 111 formed within the distal portion 115d, and in fluid communication with the fluid delivery lumen 116d. The proximal end (not shown) of the elongate member may be fluidly connected to an external fluid source (not shown) configured to deliver pressurized fluid through the lumen 116d such that fluid exits inward-facing aperture(s) 118d, e.g., as a high-pressure jet or spray 119d. The recess 111 may ensure that only necrotic debris captured therein is acted upon by the high-pressure jet or spray 119d, thereby allowing the distal end 114d of the necrosectomy tool to be placed in direct contact with the tissue wall of the necrotic pocket while protecting the underlying tissue from damage that might lead to a bleeding event. Although the necrosectomy tool of FIG. 4 includes six inward-facing apertures 118d evenly spaced about an inner wall of the recess 111, in various embodiments the elongate member 410 may include any number, arrangement, pattern and/or spacing of inward-facing apertures 118d about the inner wall of the recess. For example, the inward-facing aperture(s) may be positioned substantially perpendicular (e.g., approximately 90 degrees) relative to the longitudinal axis of the elongate member. The angle of the inward-facing aperture(s) may vary as necessary (e.g., approximately 70 degrees, approximately 80 degrees, approximately 100 degrees, approximately 110 degrees) to provide a broader or narrower stream of high-pressure fluid within the recess or pocket 111.

Figure 5:
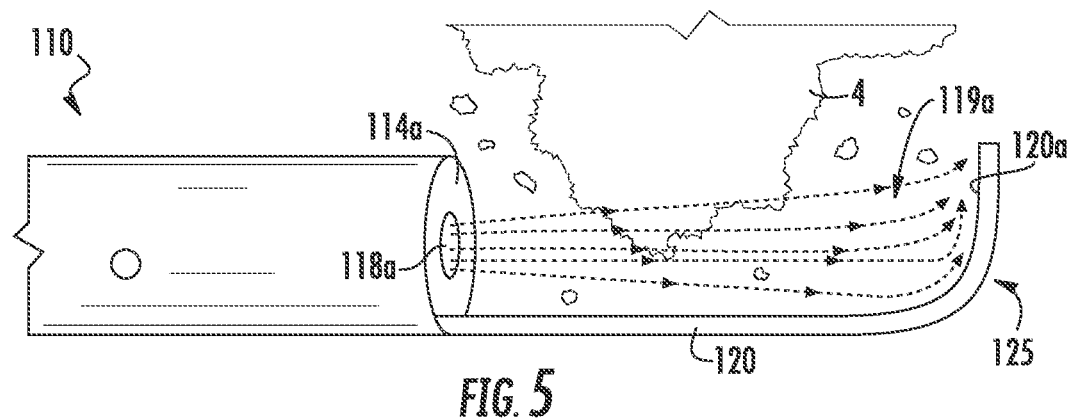
FIG. 5 provides a perspective view of a necrosectomy tool comprising an arm extending distally beyond the front-facing fluid delivery aperture of FIG. 1, according to one embodiment of the present disclosure.

Referring to FIG. 5, the elongate member 110 of FIG. 1 may further include an arm 120 extending distally beyond the distal end 114a. A distal portion 125 of the arm 120 may curve or bend to provide a planar surface 120a positioned directly opposite (e.g., perpendicular to the longitudinal axis of the elongate member) to the front-facing aperture 118a. The planar surface 120a may provide a distal backstop against which the pressurized fluid 119a may impact, thereby at least partially blocking contact of the pressurized fluid, e.g., as a high-pressure jet or spray 119a, with the tissue wall of the necrotic pocket. The front-facing aperture 118a and planar surface 120a may be separated by a sufficient distance (e.g., approximately 0.5 cm to 3.0 cm; more preferably approximately 1.0 cm to 2.0 cm) to allow necrotic debris 4 to be acted upon by the high-pressure jet or spray 119a. In one embodiment, the arm 120 may be slidably disposed within a groove or lumen (not shown) formed within a distal portion 115a of the elongate member such that the distance between the front-facing aperture 118a and planar surface 120a may be varied depending on the size and/or consistency of the necrotic debris. For example, the arm 120 may be distally extended to allow relatively large "chunks" of necrotic debris to fit between the planar surface 120a and front facing aperture 118a. Similarly, the arm 120 may be proximally retracted to accommodate relatively small "chunks" of necrotic debris. The arm 120 may also be rotatable relative to the distal end 114*a* of the elongate member such that the planar surface 120*a* is positioned in front of the front-facing aperture 118*a* when, e.g., the distal end 114*a* of the elongate member 110 is in the vicinity of a delicate or highly vascularized portion of the necrotic pocket, and then rotated out of the path of pressurized fluid when a more aggressive fluid flow is required or acceptable. In addition, or alternatively, the planar surface 120*a* of the arm 120 may be positioned (at various distances) in front of the front-facing aperture 118*a* to direct/deflect the otherwise distally directed flow of high-pressure fluid 119*a* at an angle within a specific portion of the necrotic pocket. For example, the planar surface may deflect the high-pressure fluid within the necrotic pocket at an angle (e.g., approximately 70 degrees, approximately 80 degrees, approximately 90 degrees, approximately 100 degrees, approximately 110 degrees) relative to the longitudinal axis of the elongate member.

In addition, or alternatively, the planar surface 120*a* of the arm 120 may include one or more apertures (not shown) configured to remove at least a portion of the fluid and/or necrotic debris from within the necrotic pocket under suction/vacuum to an external collection container through a separate suction lumen (not depicted) running through or along the elongate member 110. The ability to remove a portion of the fluid exiting the front-facing aperture 118*a* may prevent the necrotic pocket from becoming completely filled with fluid, and possibly rupturing and/or stretching to the point that a bleeding event occurs. The suction/vacuum force applied to the one or more apertures in the planar surface 120*a* of the arm 120 may be increased or decreased as necessary to remove more or less fluid and/or debris from the necrotic pocket. For example, the suction force may be increased to remove and further disrupt necrotic debris dislodged by the high-pressure jet or spray through the suction lumen to the collection container. Removing such dislodged debris from within the necrotic pocket may allow the high-pressure jet or spray to act upon the remaining debris without obstruction.

Figure 6:
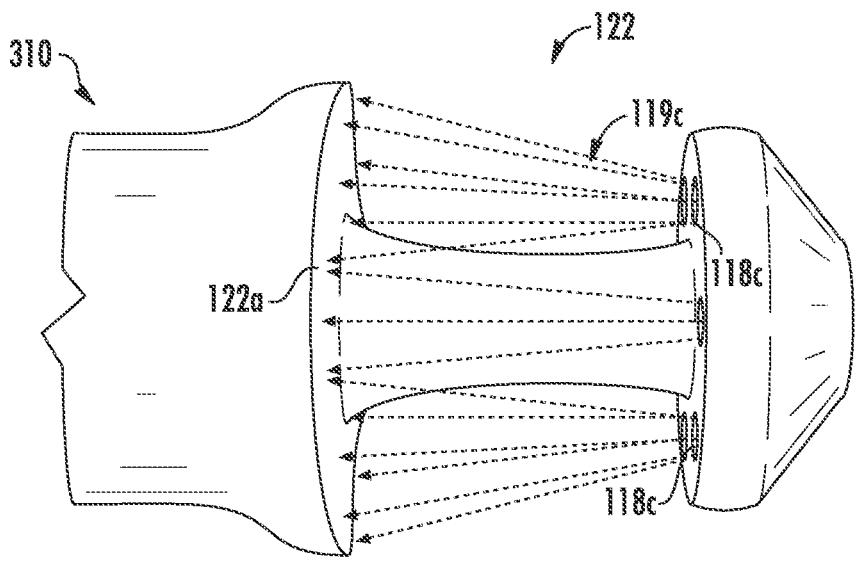
FIG. 6 provides a perspective view of a necrosectomy tool comprising an arm positioned proximal to the rear-facing fluid delivery apertures of FIG. 3, according to one embodiment of the present disclosure.

Referring to FIG. 6, the elongate member 310 of FIG. 3 may further include a circumferential recessed portion 122 (e.g., annular ring, etc.) formed within the distal portion 115*c* and proximal to the one or more rear-facing apertures 118*c*. The circumferential recessed portion 122 may define a planar surface 122*a* directly opposite the rear-facing aperture(s) 118*c* to provide a proximal backstop against which the pressurized fluid, such as high-pressure jet or spray 119*c*, may contact, thereby at least partially blocking contact of the high-pressure jet or spray 119*c* with the tissue wall of the necrotic pocket. In one embodiment, the planar surface 122*a* may include a diameter that is greater than the diameter of the elongate member 310 to provide an increased surface area for the pressurized fluid to contact, thereby minimizing direct contact of the pressurized fluid with the tissue wall. The rear-facing aperture(s) 118*c* and planar surface 122*a* may be separated by a sufficient distance (e.g., approximately 0.5 cm to 3.0 cm; more preferably approximately 1.0 cm to 2.0 cm) to allow necrotic debris to be acted upon by the high-pressure jet or spray.

In any of the embodiments of FIGS. 1-6, the pressure at which the fluid, e.g., as jet or spray 119*a-d*, exits the fluid delivery apertures(s) 118*a*-118*d* may be manually or automatically controlled (e.g., increased or decreased) by varying the flow rate of the fluid through the lumen 116*a-d*. Any of the systems described herein may include a console which connects the necrosectomy tool to the fluid source, and optionally to a vacuum or suction source for removal of the necrotic debris. The console may include, e.g., a controller by which the velocity of the fluid may be varied. For example, the velocity settings may be pre-programmed or user selectable. In addition, or alternatively, the diameter of the opening of each fluid delivery aperture(s) may be individually adjustable to provide a higher (e.g., by decreasing the diameter of the opening) or lower (e.g., by increasing the diameter of the opening) pressure jet or spray. The duration of the high-pressure jet or spray may also be adjusted by the medical professional based on the requirements of the medical procedure. For example, the high-pressure jet or spray may be delivered as a continuous spray that is turned on/off at the discretion of the medical professional, or as a series "pulses" delivered at predetermined intervals.

Although the apertures and lumens of FIGS. 1-6 are described in the context of fluid delivery, in various embodiments, direction of fluid flow through such lumens and apertures may be intermittently reversed to provide suction of the fluid and/or necrotic debris from within the necrotic pocket. For example, a high-pressure jet or spray may be introduced into the necrotic pocket as discussed above to disrupt some or all of the necrotic debris therein. Suction may then be applied to draw the fluid and/or necrotic debris into the aperture(s) and through the lumen for removal. Suction may be increased as necessary to force large pieces of debris through the apertures. If the aperture(s) become plugged with large pieces of debris, fluid may be re-introduced through the lumen to dislodge/expel the debris. An intermittent pattern of fluid delivery followed by fluid/debris removal under suction may be repeated as necessary to clean the necrotic pocket.

A variety of biologically inert fluids may be used to facilitate efficient removal of necrotic fluid and debris from the necrotic pocket. For example, the disruption/dissolution of necrotic debris may be enhanced by introducing a high-pressure jet or spray of heated fluid (e.g., approximately 70° C. or more, approximately 80° C. or more, approximately 90° C. or more). The fluid may also include a variety of antimicrobial or antibiotic agents to promote sterilization or disinfection of the necrotic pocket. In addition, or alternatively, the fluid may include one or more chemical solutions (e.g., hydrogen peroxide, alcohol, etc.) and/or enzymes (e.g., proteinases, hyaluronidase, etc.) to further facilitate disruption and removal of the necrotic debris.

Mechanical Disruptors

In one embodiment, the present disclosure relates to a necrosectomy tool which utilizes a tissue disrupting element carried on or about the distal end of a delivery device to facilitate disruption and removal of necrotic debris without disrupting or damaging the tissue wall of the necrotic pocket. These mechanical disruptors may find beneficial use for removal of necrotic debris of various consistency, including, but not limited to, high viscosity or "non-flowable" necrotic debris that requires physical disruption (e.g., pulverization, blending, maceration, etc.) to facilitate efficient clearance from the necrotic pocket.

Referring to FIGS. 7A-7C, a necrosectomy tool of the present disclosure may include an elongate member 710 comprising a tissue disrupting element 140*a* with one or more cutting members 146*a* disposed around a support shaft 149, wherein the support shaft 149 is rotationally attached to the distal end 214*a* of the elongate member 710. The cutting member(s) 146*a* may include proximal end 147*a* attached to a proximal end 149*a* of the support shaft 149, and a distal end 148*a* attached to a distal end 149*b* of the support shaft 149. The cutting member(s) 146*a* are configured to move between a delivery configuration (FIG. 7B) in which the cutting members are disposed substantially parallel to the support shaft 149, and a deployed configuration (FIG. 7C) in which the cutting member(s) bow radially outward. A variety of deployment mechanisms are available for moving the cutting member(s) between the delivery and deployed configuration. For example, the cutting member(s) 146a may be slidably disposed within a groove or lumen (not shown) formed within the distal portion 215a of the elongate member 710. When constrained within the groove or lumen, the cutting member(s) may be held substantially parallel to the support shaft 149. The support shaft 149 may be advanced distally beyond the distal end 214a of the elongate member 710 such that the cutting member(s) are released from constraint within the groove or lumen (FIG. 7B), thereby allowing the cutting member(s) to bow radially outward (FIG. 7C). In this and other embodiments, the distal end 214a of the elongate member may include an atraumatic tip 213 (e.g., rounded end) to further minimize or prevent trauma to the tissue wall of the necrotic pocket. The atraumatic tip 213, and elongate member, may be formed from a variety of soft or compliant materials as are known in the art (e.g., soft plastics, soft rubber, neoprene, and the like).

Figure 8:
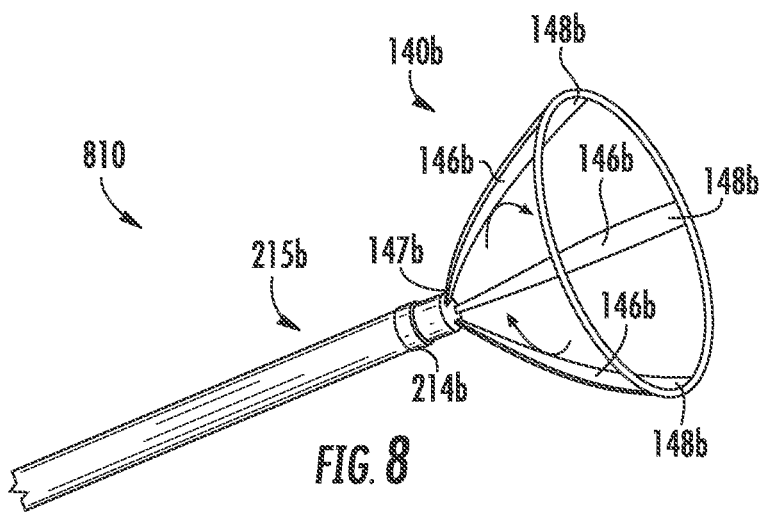
FIG. 8 provides a perspective view of a necrosectomy tool comprising a plurality of cutting elements, according to one embodiment of the present disclosure.

Referring to FIG. 8, a necrosectomy tool of the present disclosure may include an elongate member 810 comprising a tissue disrupting element 140b with one or more cutting members 146b rotationally attached to a distal end 214b of the elongate member, wherein a proximal end 147b of each cutting member(s) is attached to the distal end 214b, and a distal end 148b of each cutting member(s) is unattached and extends distally beyond the distal end 214b in a basket or funnel-like configuration. The cutting member(s) 146b are configured to move between a delivery configuration (not shown) in which the cutting members are retracted within a lumen formed within the distal portion 215b, and a deployed configuration (FIG. 8) when the cutting members are released from constraint within the lumen. In one embodiment, a cylindrical ring may be attached to the distal end 214b of each cutting member 146b such that proximally retracting (e.g., into the elongate member) a control wire connect to the cylindrical ring may allow the cutting members to move together to grasp and/or disrupt necrotic debris caught between the cutting members.

Figure 9A:
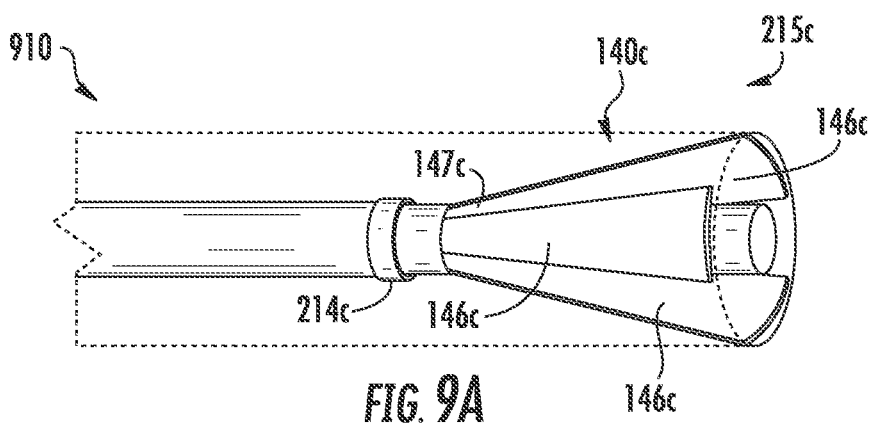
FIGS. 9A-9B provide perspective views of a necrosectomy tool comprising a plurality of cutting elements configured to move between a delivery configuration (FIG. 9A) and deployed configuration (FIG. 9B), according to one embodiment of the present disclosure.
Figure 9B:
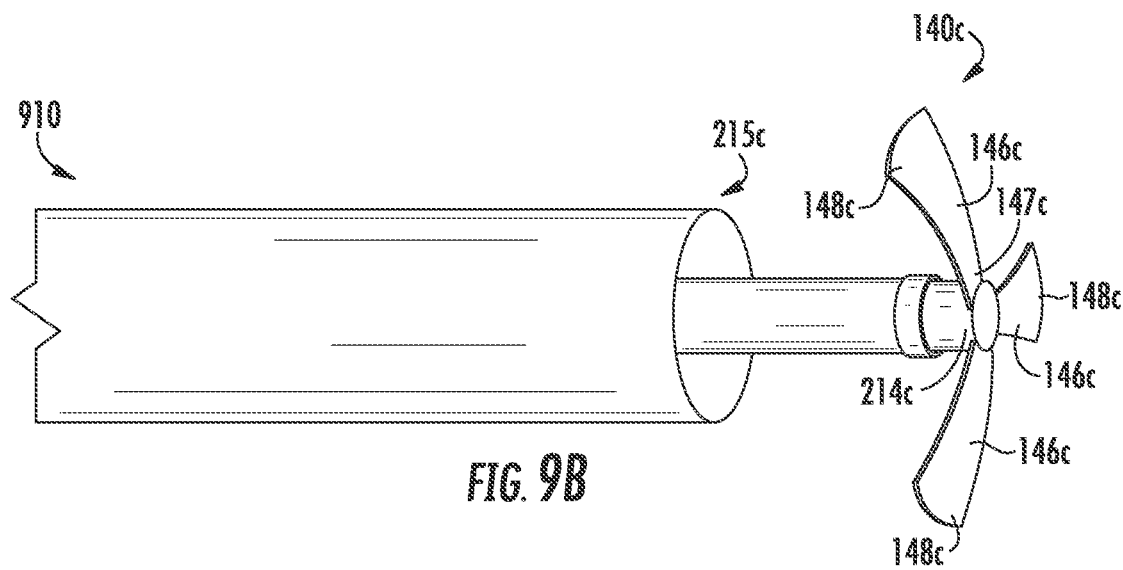

Referring to FIGS. 9A-9B, a necrosectomy tool of the present disclosure may include an elongate member 910 comprising a tissue disrupting element 140c with one or more cutting members 146c rotationally attached to a distal end 214c of the elongate member, wherein a proximal end 147c of each cutting member(s) is attached to the distal end 214c, and a distal end 148c of each cutting member(s) is unattached and bends or curves proximally beyond the distal end 214c in an umbrella-like configuration. The cutting member(s) 146c are configured to move between a delivery configuration (FIG. 9A) in which the cutting members are retracted within a lumen formed within the distal portion 215c of the elongate member, and a deployed configuration (FIG. 9B) in which the cutting members are released from constraint within the lumen.

In any of the embodiments of FIGS. 7A-9B, one or both sides of the cutting member(s) 140a-c may include a variety of cross-sectional forms defining a cutting surface (e.g., sharpened edge, abrasive surface, serrations, teeth, etc.) configured to engage and disrupt necrotic debris as the cutting member(s) rotate within the necrotic pocket. The distal end 214a-c of the elongate member may be configured to rotate at variety of speeds, in either a clockwise or counter-clockwise direction, at the discretion of the medical professional. For example, the proximal end (not shown) of the delivery device may be operably connected to a motor drive unit (MDU) to allow the medical professional to control the speed and/or direction of rotation of the cutting member(s).

Figure 10:
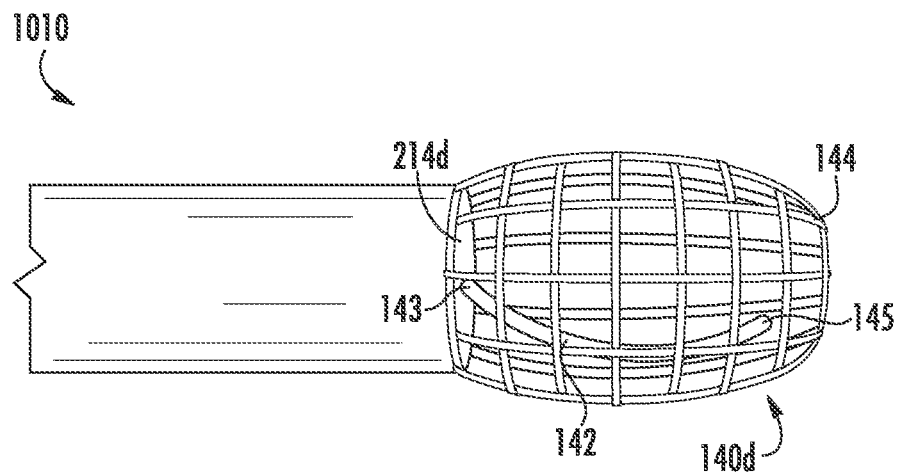
FIG. 10 provides a perspective view of a necrosectomy tool comprising a cutting element disposed within a cage, according to one embodiment of the present disclosure.

Referring to FIG. 10, a necrosectomy tool of the present disclosure may include an elongate member 1010 comprising a tissue disrupting element 140d with a cutting element 142 disposed within a cage 144. A proximal end 143 of the cutting element 142 may be rotationally attached to the distal end 214d of the elongate member such that an unattached distal end 145 of the cutting element is free to move (e.g., gyrate, undulate, rotate) at high speed within the cage 144. For example, the cutting element 142 may include a flexible wire or polymer fiber that "whips" or "flops" around within the cage with sufficient velocity and/or force that any necrotic debris that enters through the open weave of the cage 144 is pulverized or macerated. The ability of the cage 144 to contain the cutting element 142 may allow the outer surface of the cage to be placed in direct contact with the tissue wall of the necrotic pocket while protecting the underlying tissue from damage that might lead to a bleeding event. In various embodiments, the cage may include a variety of shapes and/or configurations to allow the entry of larger or smaller pieces of necrotic debris.

Figure 11:
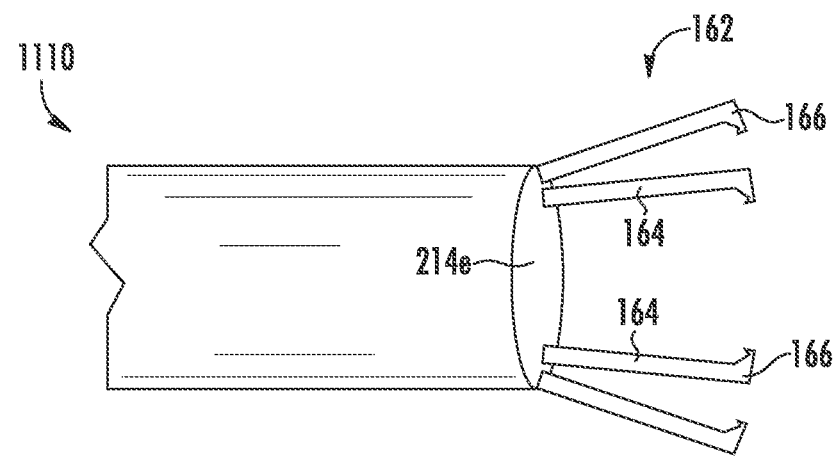
FIG. 11 provides a perspective view of a necrosectomy tool comprising a plurality of grasping elements, according to one embodiment of the present disclosure.

Referring to FIG. 11, a necrosectomy tool of the present disclosure may include an elongate member 1110 comprising one or more grasping elements 162 configured to engage large pieces of necrotic debris. For example, the grasping element(s) 162 may include opposing sets of arms 164 disposed on opposite sides of the distal end 214e of the elongate member and configured to move between an open configuration (FIG. 11) and a closed configuration (not shown) to grip and secure large "chunks" of necrotic debris for removal from the necrotic pocket. The arms 164 may include one or more hooks, barbs or fingers 166 to penetrate and engage the necrotic debris for efficient removal. In addition, or alternatively, the arms 164 may be used in a scissor-like manner to break up large portions of necrotic debris into smaller (e.g., more manageable) sizes for removal from the necrotic pocket.

Figure 12A:
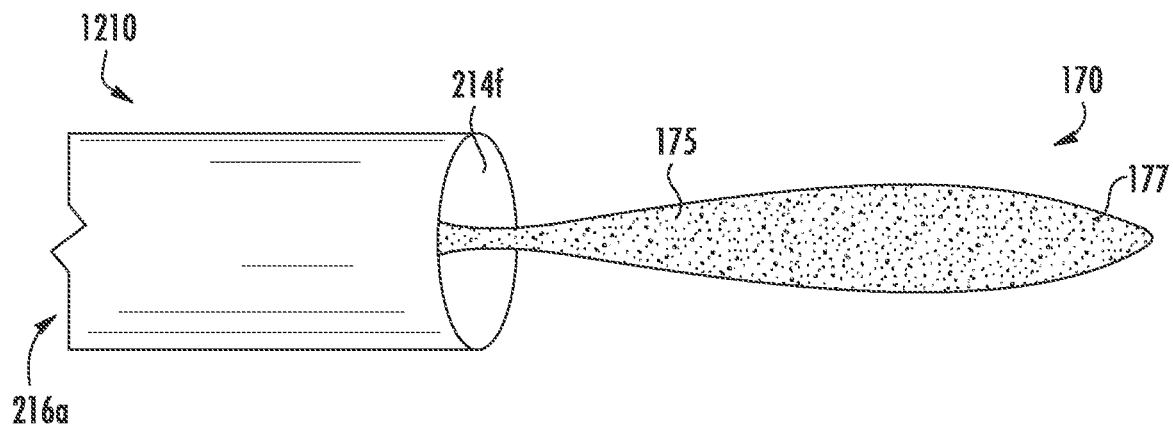
FIGS. 12A-12B provide perspective views of a necrosectomy tool comprising an expandable member configured to move between an unexpanded/delivery configuration (FIG. 12A) and an expanded/deployed configuration (FIG. 12B), according to one embodiment of the present disclosure.
Figure 12B:
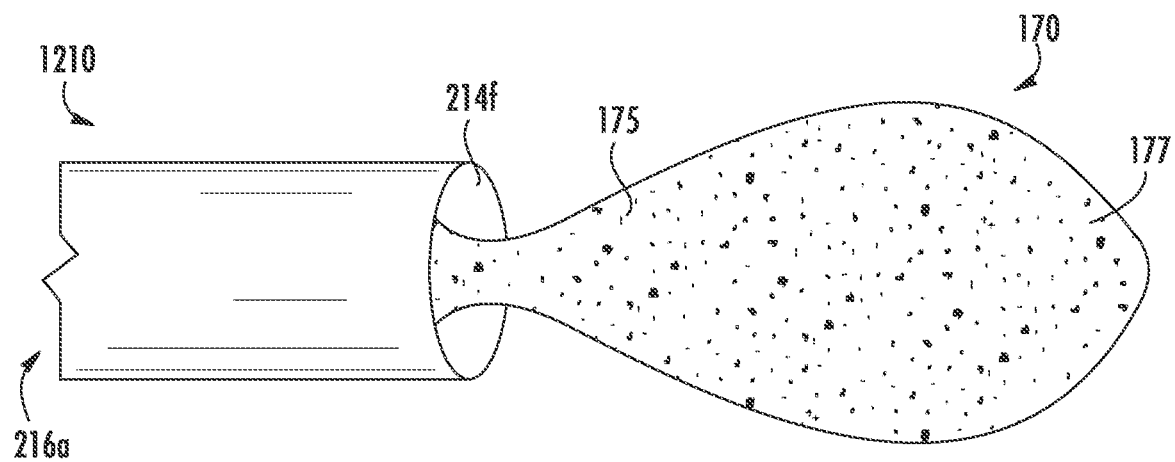

Referring to FIGS. 12A-12B, a necrosectomy tool of the present disclosure may include an elongate member 1210 comprising a proximal end (not shown), a distal end 214f and a lumen 216a extending therebetween. An expandable member 170 (e.g., balloon) moveable between an unexpanded (e.g., deflated/delivery) configuration and expanded (e.g., inflated/deployed) configuration may be rotationally attached to the distal end 214f of the elongate member. The expandable member 170 may move from the unexpanded configuration (FIG. 12A) to the expanded configuration (FIG. 12B) by flowing an inflation fluid (e.g., air, saline, etc.) from an external fluid source (not shown) through the lumen 216a into an interior region 175 of the expandable member. Similarly, the expandable member 170 may move from the expanded configuration to the unexpanded configuration by returning the inflation fluid from the interior region 175 to the external fluid source through the lumen 216a. The expandable member 170 may include a course or abrasive outer surface 177 configured to engage and disrupt necrotic debris as the expandable member rotates within the necrotic pocket. For example, the outer surface 177 of the expandable member 170 may be entirely or partially covered or embedded with particles (e.g., diamond particles, flakes or dust) which impart a rough texture to the expandable member when in the expanded configuration. The expandable member may be formed from a variety of semi-compliant or non-compliant materials, as are commonly known in the art, such that the expandable member assumes a pre-determined shape within the necrotic pocket, thereby preventing possible complications resulting from over-expansion within the necrotic pocket.

In any of the embodiments of FIGS. 1-12B, necrotic debris disrupted by either pulsatile flow (FIGS. 1-6) or a tissue disrupting element (FIGS. 7A-12B) may circulate within the necrotic pocket and flow/exit around the elongate member into the gastrointestinal tract for safe removal by the body's natural course. In addition, or alternatively, any of the embodiments of FIGS. 1-12B may further include a separate lumen configured to remove necrotic debris and fluid from within the necrotic pocket under suction. For example, the suction lumen may be integrally formed within the elongate member and extend between the distal and proximal ends. The suction lumen may also be introduced as a separate component (e.g., drainage tube) introduced alongside, or attached to, an outer surface of, the elongate member. To facilitate gentle removal of necrotic debris, in embodiments where there is a suction lumen independent of the fluid delivery lumen, the suction lumen may include an inner diameter that is larger than an inner diameter of the fluid delivery lumen. For example, the diameter of the suction lumen may be at least 5 times greater than the fluid delivery lumen. In addition to removing necrotic debris through the suction lumen, large pieces of necrotic debris that are too large to fit within the suction lumen may become attached to or lodge against the distal opening of the suction lumen and removed from the necrotic pocket and deposited (e.g., dislodged) within the gastrointestinal tract. The suction lumen may also be used as an aspiration lumen through which a bolus of wash solution may be gently introduced into the necrotic pocket as a wash or lavage step after the majority of the necrotic debris has been removed by the more aggressive pressurized fluid flow or tissue disrupting elements. In various embodiments, any of the disclosed flow disruptors and mechanical disrupters may be combined into a single device, with or without suction capability.

Figure 13:
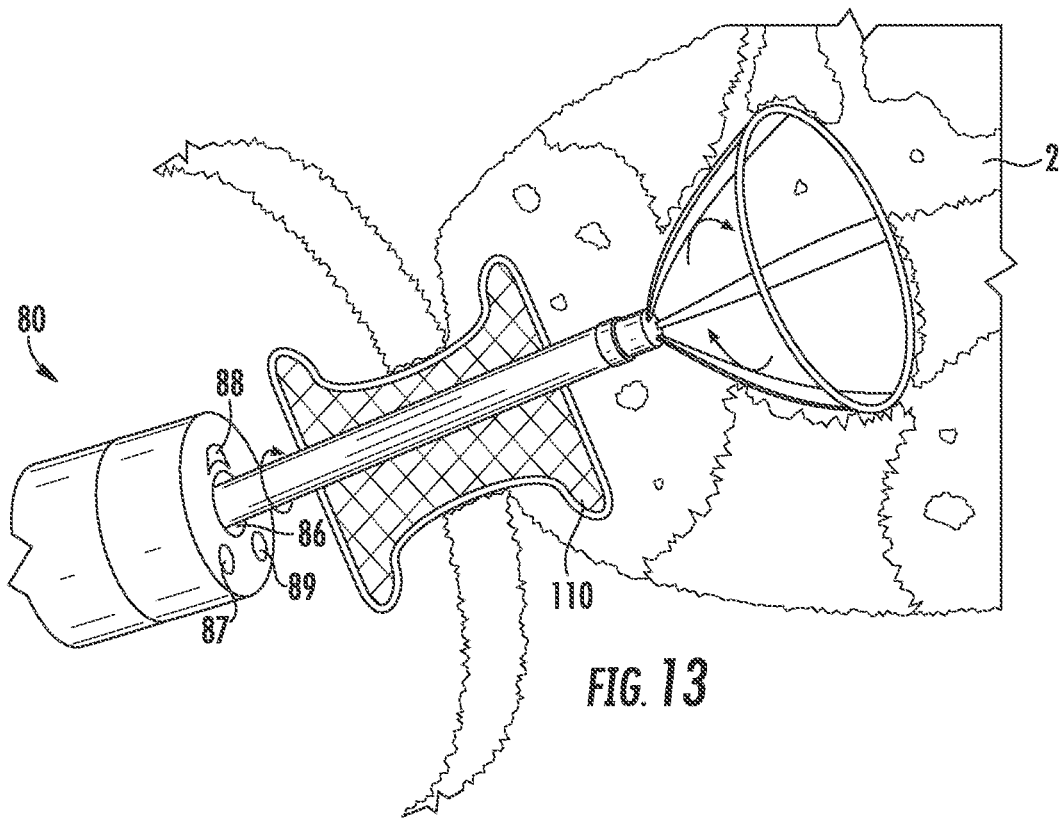
FIG. 13 provides a perspective view of a system comprising a necrosectomy tool extending through an endoscope working channel into a necrotic pocket, according to one embodiment of the present disclosure.

In one embodiment, a necrosectomy tool of the present disclosure may be introduced into the necrotic pocket in the absence of a delivery device (e.g., endoscope, etc.). In such an embodiment, the necrosectomy tool may include steering capability and a camera and light source (not depicted) to allow the medical professional to visualize the steerable necrosectomy tool, necrotic debris and tissue wall of the necrotic pocket. Alternatively, referring to FIG. 13, any of the necrosectomy tools of the present disclosure may be introduced into a necrotic pocket 2 through a first working channel 86 of an endoscope 80 and a stent 100 disposed between the adjacent tissue layers of the necrotic pocket and an adjacent body lumen (e.g., duodenum, etc.). The endoscope may also include a second working channel 87 through which necrotic debris and fluid may be removed under suction and/or a bolus of wash solution may be introduced to flush the necrotic pocket. The distal end of the endoscope 80 is steerable and includes a camera 88 and light source 89 to visualize the necrosectomy tool, necrotic debris and tissue wall of the necrotic pocket. In any of the embodiments of tools described here, whether for use alone or in conjunction with an endoscope, the elongate member may be provided with independent steering capability.

In use, and by way of example, a necrosectomy tool of the present disclosure may be introduced into a body lumen through a body opening (e.g., mouth, rectum, etc.) and positioned adjacent to a tissue wall of the body lumen. The necrosectomy tool may then be advanced through a previously formed opening within the tissue wall and positioned within a necrotic pocket adjacent to the body lumen. Alternatively, the necrosectomy tool may include a sharpened distal end or other suitable tissue cutting element (e.g., electrocautery tip, knife, blade, etc.) configured to allow the necrosectomy tool to be advanced through (e.g., puncture) the tissue wall. The pulsatile flow (FIGS. 1-6) or a tissue disrupting element (FIGS. 7A-12B) of the necrosectomy tool may then be activated such that necrotic debris within the necrotic pocket is disrupted and removed, as discussed above. The user may manipulate the necrosectomy tool within the necrotic pocket, e.g., using ultrasound guidance or direct visualization with a camera, as necessary to remove the necrotic debris from within the necrotic pocket. Once the user has determined that all, or a sufficient portion, of the necrotic debris has been removed, the necrosectomy tool may be retracted through the opening into the body lumen and removed from the body. The opening may then be sealed (e.g., sutured, stapled, cauterized, etc.) to restore the integrity of the tissue wall.

Drainage

In one embodiment, the present disclosure relates to a necrosectomy tool which utilizes a dual-lumen drainage catheter to actively circulate and remove necrotic debris without disrupting or damaging the tissue wall of the necrotic pocket. These drainage catheters may find beneficial use alone or in combination with other of the tool embodiments described above, for removal of necrotic debris of various consistency, including, but not limited to, low or medium viscosity necrotic debris (e.g., "flowable" necrotic debris) that does not necessarily require physical disruption to facilitate efficient clearance from the necrotic pocket.

Figure 14:
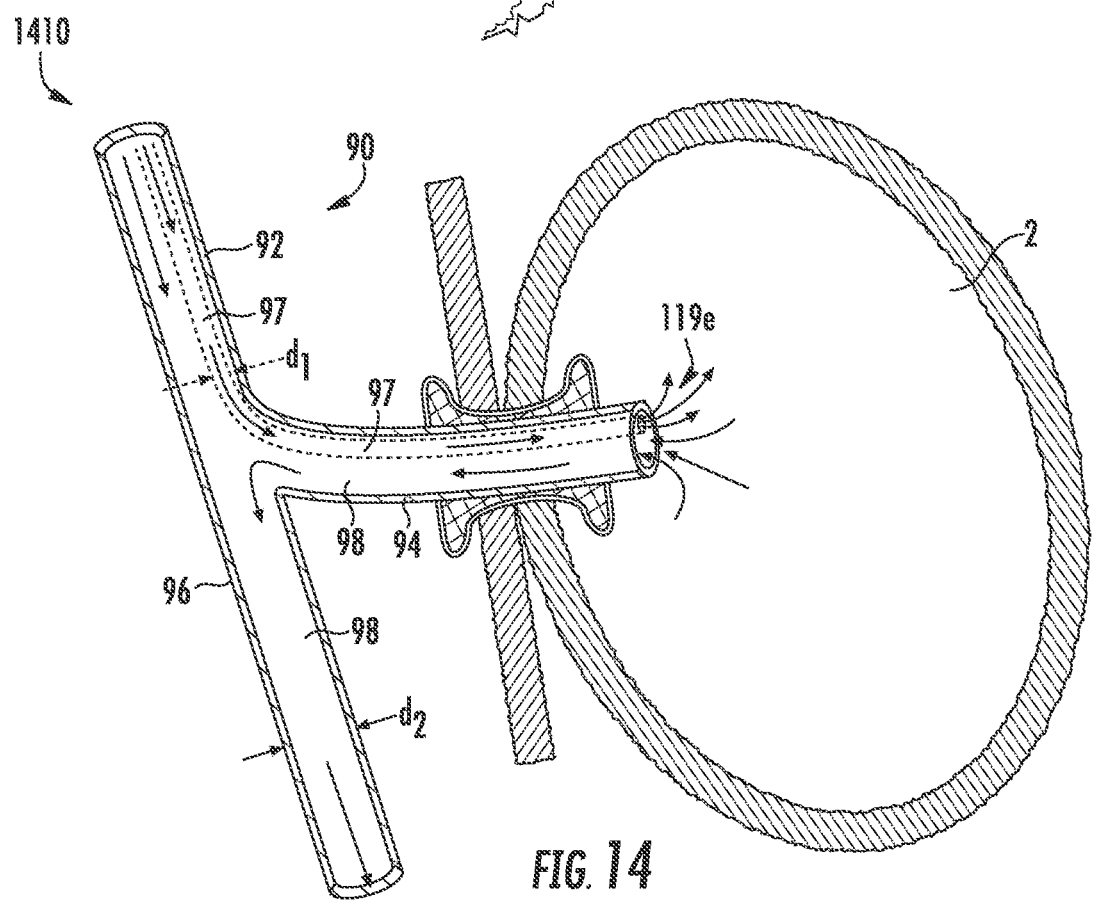
FIG. 14 provides a perspective view of a drainage catheter extending into a necrotic pocket, according to one embodiment of the present disclosure.

Referring to FIG. 14, a necrosectomy tool of the present disclosure may include a drainage catheter 90 comprising a first tubular portion 92, a second tubular portion 94 and third tubular portion 96, wherein the first and second tubular portions 92, 94 define a delivery lumen 97 (e.g., fluid delivery lumen, inflow lumen, etc.) and the first, second and third tubular portions 92, 94, 96 define a bifurcated removal lumen 98 (e.g., fluid removal lumen, outflow lumen, etc.). The delivery lumen 97 may include a diameter $d_1$ configured to deliver pressurized fluid from an external fluid source (not shown) into the necrotic pocket, e.g., as a high-pressure jet or spray 119e. The removal lumen 98 may include a diameter $d_2$ greater than the diameter $d_1$ to facilitate gentle removal of necrotic debris from the necrotic pocket. In use, and by way of example, the first tubular portion 92 may exit from the patient's nose or mouth, the second tubular portion 94 may extend into the necrotic pocket 2 (e.g., through a stent 100) and the third tubular portion 96 may extend into the patient's gastrointestinal tract. A pressurized fluid (e.g., isotonic saline, hydrogen peroxide, etc.) may be actively delivered (e.g., pumped) through the delivery lumen 97 defined by the first and second tubular portions 92, 94 to circulate within the necrotic pocket. Pressurized fluid may also be actively delivered through the bifurcated removal lumen 98 defined by the first and third tubular portions 92, 96 such that negative pressure generated across the bifurcated junction provides a siphoning/suction effect through the bifurcated removal lumen 98 defined by the second tubular portion 94, thereby drawing necrotic debris and fluid circulating within the necrotic pocket into the gastrointestinal tract for safe removal by the body's natural course. Alternatively, the necrotic debris and fluid may be removed from the body through a separate catheter and/or working channel of an endoscope.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system, comprising:
an elongate member, comprising:
a distal end, and
a proximal end; and
a tissue disrupting element on the distal end of the elongate member, the tissue disrupting element including a plurality of cutting members comprising a cutting edge, the plurality of cutting members disposed about a support shaft extending from the elongate member, wherein the plurality of cutting members include a proximal end directly attached to a proximal portion of the support shaft, and wherein a respective one of the plurality of cutting members extend from the elongate member, and the respective one of the plurality of cutting members is configured to move between a delivery configuration in which the respective one of the plurality of cutting members is constrained and a deployed configuration in which the respective one of the plurality of cutting members bows radially outward, and
wherein the elongate member comprises a plurality of grooves, each of the plurality of grooves configured to slidingly accept a corresponding member of the plurality of cutting members.

2. The system of claim 1, wherein the plurality of cutting members include a distal end attached to a distal end of the support shaft.

3. The system of claim 1, wherein the plurality of cutting members are configured to transition between the delivery configuration and the deployed configuration by slidably translating the support shaft with respect to the distal end of the elongate member.

4. The system of claim 1, wherein the support shaft is rotatably coupled to the elongate member.

5. The system of claim 1, further comprising an atraumatic tip disposed on a distal end of the support shaft.

6. The system of claim 1, wherein the disrupting element comprises three cutting members circumferentially arrayed about the support shaft at a substantially equal distance from each other.

7. The system of claim 1, wherein the support shaft is slidably and rotatably disposed within a lumen of the elongate member.

8. The system of claim 1, wherein the cutting edge comprises one of a sharpened edge, an abrasive surface, a serration, and a plurality of teeth.

9. A device, comprising:
an elongate member;
a support shaft slidably disposed within the elongate member; and
a plurality of cutting members comprising a cutting edge, the plurality of cutting members having a proximal end directly coupled to the support shaft, wherein the plurality of cutting members, and wherein when the plurality of cutting members extend from the elongate member, the plurality of cutting members are configured to move between a delivery configuration in which the plurality of cutting members is constrained and a deployed configuration in which the plurality of cutting members bows radially outward,
wherein the elongate member comprises a plurality of grooves, each of the plurality of grooves configured to slidingly accept a corresponding member of the plurality of cutting members.

10. The device of claim 9, wherein the proximal end of the plurality of cutting members are coupled to a proximal portion of the support shaft and a distal end of the plurality of cutting members are coupled to a distal end of the support shaft.

11. The device of claim 9, wherein the plurality of cutting members are configured to transition between the delivery configuration and the deployed configuration by slidably translating the support shaft with respect to a distal end of the elongate member.

12. The device of claim 9, wherein the support shaft is rotatably disposed within the elongate member.

13. The device of claim 9, wherein the cutting edge comprises one of a sharpened edge, an abrasive surface, a serration, and a plurality of teeth.

14. A device, comprising:
an elongate member comprising a lumen therethrough;
a support shaft disposed within the lumen of the elongate member; and
a plurality of cutting members disposed about the support shaft, each of the plurality of cutting members having a proximal end directly coupled to the support shaft, wherein the plurality of cutting members extend from the elongate member, the plurality of cutting members are configured to move between a delivery configuration in which the plurality of cutting members are constrained and a deployed configuration in which the plurality of cutting members bow radially outward;
wherein the elongate member further comprises a plurality of grooves, each of the plurality of grooves configured to slidingly accept each corresponding member of the plurality of cutting members.

15. The device of claim 14, wherein the support shaft is slidably and rotatably disposed within the lumen of the elongate member.

16. The device of claim 14, wherein the plurality of cutting members are configured to transition between the delivery configuration and the deployed configuration by slidably translating the support shaft with respect to a distal end of the elongate member.

17. The device of claim 14, wherein each of the plurality of cutting members comprises a cutting edge.

* * * * *